(12) United States Patent
Ellis et al.

(10) Patent No.: US 7,709,251 B2
(45) Date of Patent: May 4, 2010

(54) METHOD AND APPARATUS FOR TRANSFERRING GROWTH MEDIA AND INFECTION FLUIDS TO A CELL GROWTH BAG

(75) Inventors: Samuel A. Ellis, San Diego, CA (US); Kenneth E. Holmes, Big Bear Lake, CA (US)

(73) Assignee: Scientific Plastic Products, Inc., Oceanside, CA (US)

( * ) Notice: Subject to any disclaimer, the term of this patent is extended or adjusted under 35 U.S.C. 154(b) by 1187 days.

(21) Appl. No.: 11/293,567

(22) Filed: Dec. 2, 2005

(65) Prior Publication Data
US 2007/0128081 A1 Jun. 7, 2007

(51) Int. Cl.
*C12M 1/00* (2006.01)
*C12M 1/22* (2006.01)

(52) U.S. Cl. .................................................. 435/305.1
(58) Field of Classification Search ................ 222/338; 220/421–568; 422/100; 435/305.1
See application file for complete search history.

(56) References Cited

U.S. PATENT DOCUMENTS

| | | | | |
|---|---|---|---|---|
| 3,449,210 | A | * | 6/1969 | Rohde ..................... 435/304.3 |
| 3,870,602 | A | * | 3/1975 | Froman et al. ............ 435/304.3 |
| 4,235,344 | A | * | 11/1980 | Kulle et al. .................. 215/250 |
| 4,665,035 | A | * | 5/1987 | Tunac ..................... 435/304.2 |
| 5,505,236 | A | * | 4/1996 | Grabenkort et al. ......... 141/329 |
| D460,322 | S | * | 7/2002 | Orr et al. ..................... D7/510 |

FOREIGN PATENT DOCUMENTS

| | | |
|---|---|---|
| GB | 730523 A | 5/1955 |
| GB | 2040890 A | 9/1980 |
| JP | 2004231217 A | 8/2004 |

OTHER PUBLICATIONS

Sigma Catalog, Techware Equipment, Books and Supplies, p. 2356 & 2357, 2000-2001.*

* cited by examiner

*Primary Examiner*—Walter D Griffin
*Assistant Examiner*—Shanta G Doe
(74) *Attorney, Agent, or Firm*—Stetina Brunda Garred & Brucker; Lowell Anderson

(57) ABSTRACT

A method and apparatus are provided for transferring growth media or infection fluids to a bioculture bag having Could Process fitting thereon in fluid communication with the inside of the bag. The media or fluid is placed in a flask. A cap is threaded onto the neck of the flask. The cap has a spout with an opening in a distal end of the spout and a vent hole in the cap. The spout has a tubular end in which the opening is formed, with an O-ring seal adjacent the distal end of the tubular end. The tubular end fits within the fitting and the seal forms a fluid tight seal with the fitting to allow fluid transfer to the bag in reduced time with reduced spillage. The cap is preferably used on a flask having shaped baffles in the bottom. The baffles are highest toward the centerline, and decline in height linearly toward the corners of the flask at an angle of about 9° to the horizontal. The flask is rotated about 80-180 RPM, and the baffles have leading and trailing sides in the direction of rotation that are inclined at about 32° relative to the vertical. A growth media is also provided to culture the cells in the flask.

24 Claims, 6 Drawing Sheets

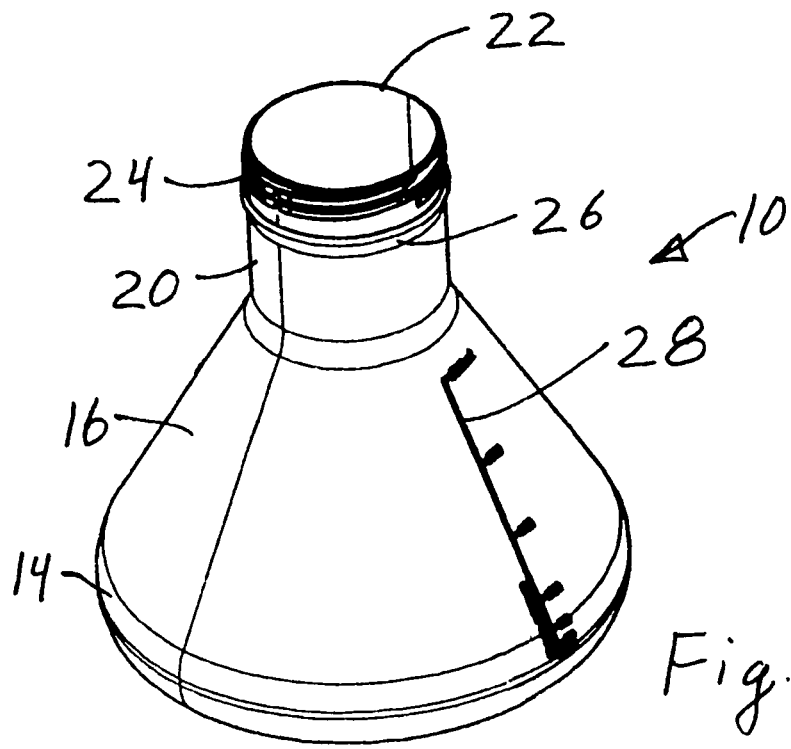
Fig. 1
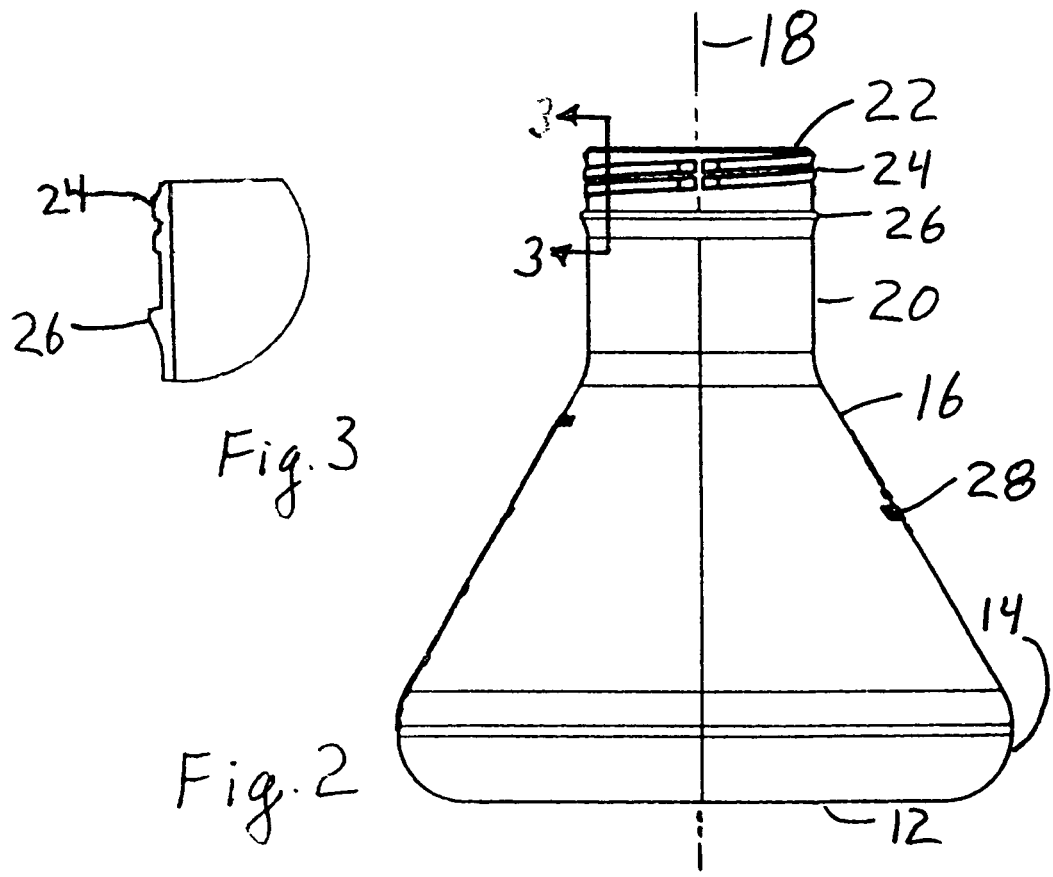
Fig. 3
Fig. 2

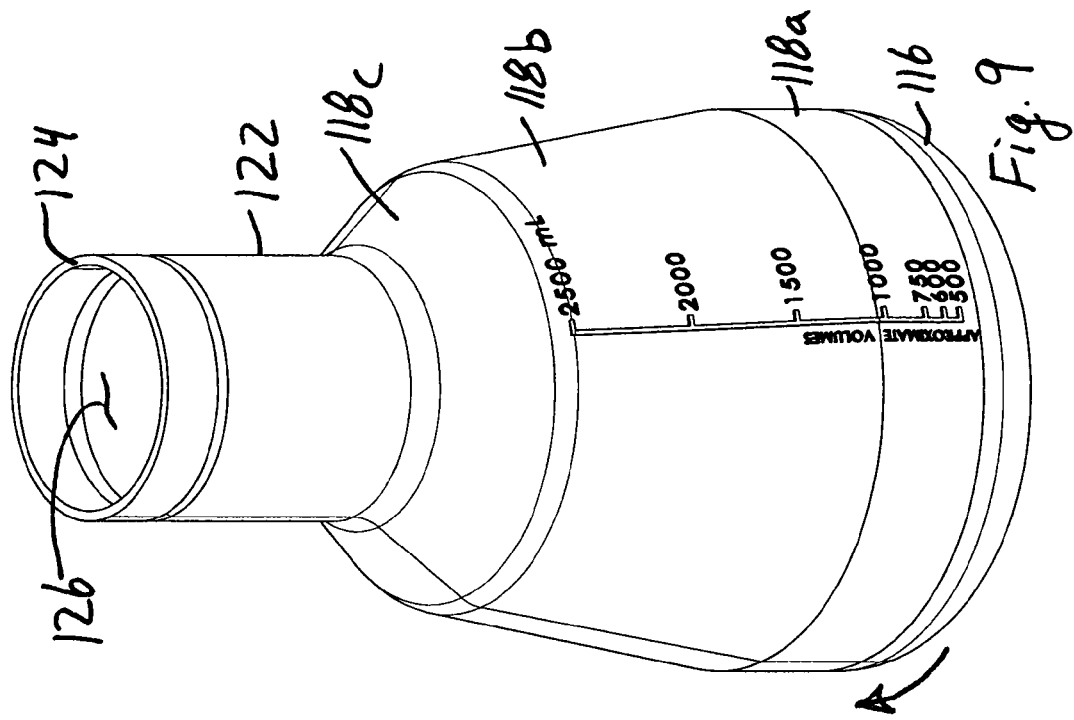
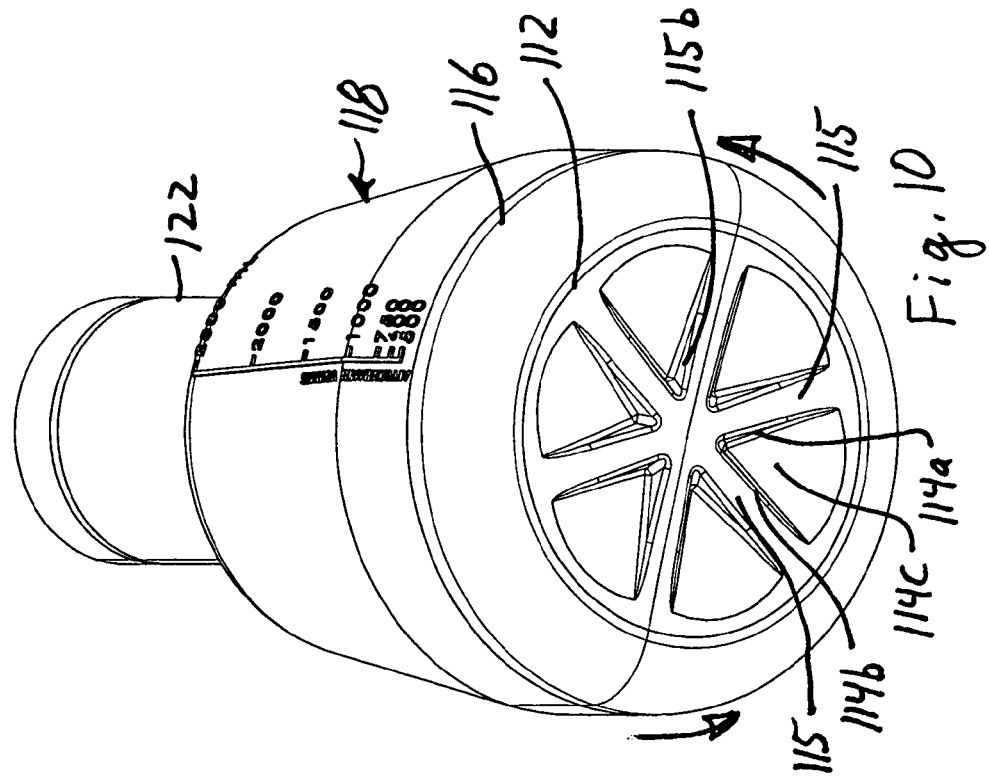

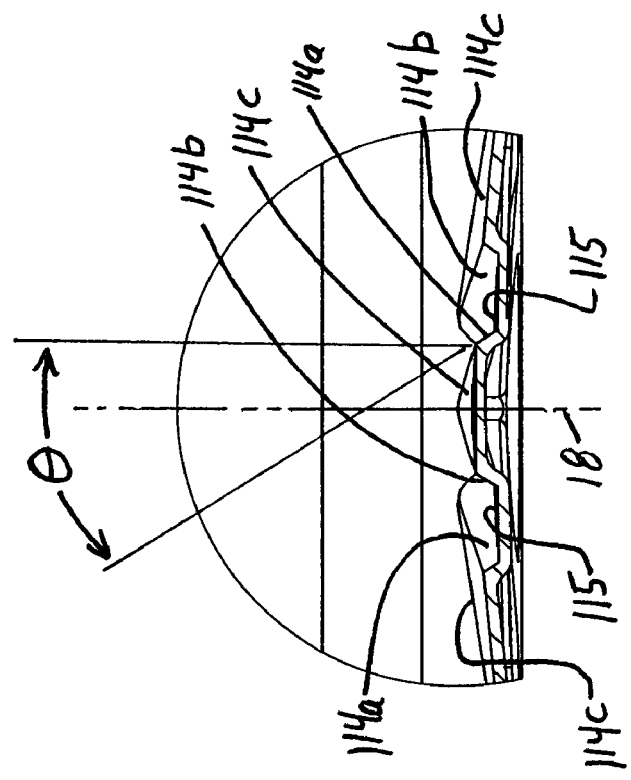
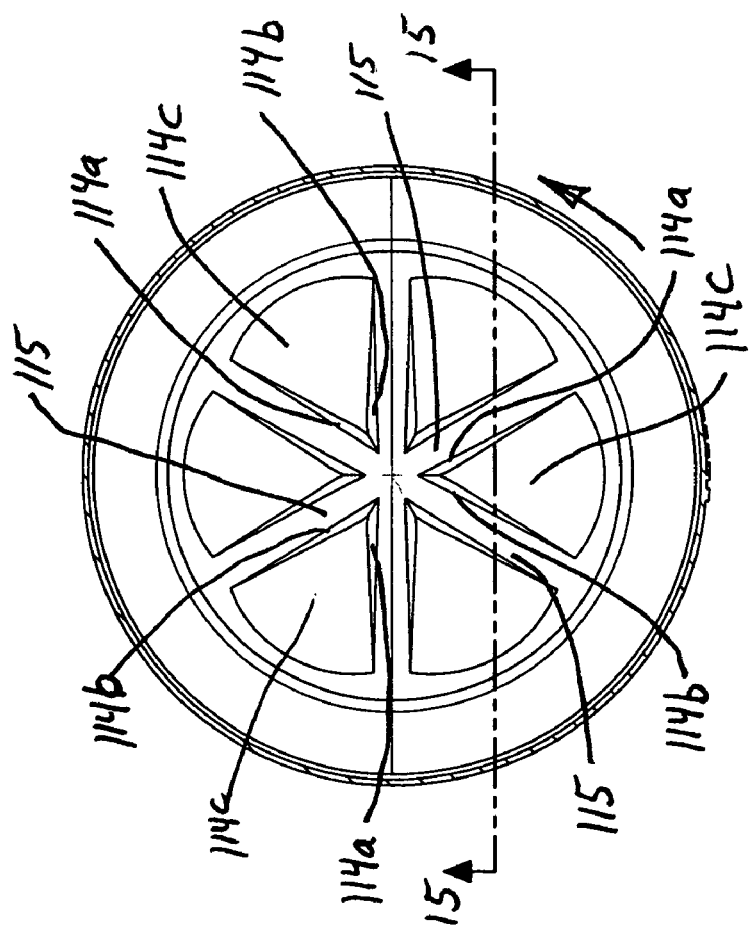
Fig. 15
Fig. 14

METHOD AND APPARATUS FOR TRANSFERRING GROWTH MEDIA AND INFECTION FLUIDS TO A CELL GROWTH BAG

BACKGROUND

Mammalian and insect cells are grown for biological testing and other uses. A starter culture is placed in a growth media such as Grace's media, which is contained in a generally flat bag ranging from 2 liters to 100 liters in volume. These bags have standard fittings on them, typically made by Colder Products Company, and covered by U.S. Pat. No. 5,052,725. The standard fitting is small, about ¼ inches (about 6 mm) in diameter. The bags are filled by pouring the Grace's media or other equivalents into the ¼ inch diameter fitting from the open lip of the bottle in which the Grace's media is shipped or addition of culture, which results in spillage of media that costs $300 to $1,000 per liter. Alternatively, the bags are filled by hand using pipettes, which takes a long time, exposes the media and culture to contamination, and still results in spillage. Pumps can also be used to transfer the growth media to the bags, but the pumps use ¼ inch tubing and fill the bag slowly and can contaminate the bags if not cleaned adequately. There is thus a need for an improved way to quickly transfer the growth media through the fitting into the bags while reducing spillage. There is a need for a direct and easy transfer of growing cells into these bags.

The bags are placed on a rocker which rocks from side to side. The bags have a smooth bottom and are rocked gently because the insect and mammalian cells rupture easily. A starting culture having a concentration of about $4 \times e^5$ is grown to $1\text{-}2 \times e^6$. Higher concentrations are desirable, and shorter times are also desirable as it decreases processing time. There is thus a need for a way to culture these cells to higher densities, and to do so in a shorter time.

These cells are often infected with a virus through smaller, ⅛ inch diameter ports (about 3 mm dia.) provided with the bag. Cell growth is continued for 48-72 hours after infection, at which time the cells are harvested. But the cells typically require a viability of about 90% or more to make harvesting viable. There is thus a need for a way to more consistently grow cells with not only desired viability, but higher viability.

SUMMARY

A pouring flask, preferably hand held, is provided with a wide mouth to allow increased fluid flow and ease of handling. The wider mouth also makes it easier to pour a growth media, such as Grace's media, into the flask without spilling. The flask has a neck covered by a cap that has a spout configured to mate with the standard Coulter fitting of ¼ inch diameter is provided. A seal on the spout mates with the fitting to reduce spillage. An O-ring seal is believed suitable. The spout has a vent hole to provide a more continuous flow while reducing contamination. A ring seal is provided inside the cap and interposed between the cap and the rim of the flask, in order to provide a fluid tight seal between the cap and flask. Preferably, the ring seal is held in place between a ring that depends from the spout, and a skirt formed on a periphery of the spout. The inside of the skirt is preferably threaded to engage mating threads on the outside of the neck of the pouring flask.

In one aspect there is advantageously provided a fluid transfer mechanism for use with a bioculture bag having a fitting thereon in fluid communication with the inside of the bag. The mechanism includes a cap having a spout with an opening in a distal end of the spout. The cap also has a peripheral cylindrical skirt with internal threads on the skirt and a vent hole in the cap. The spout has a tubular end in which the opening is formed, with a seal on the distal end. The seal encircles the tubular end. The tubular end is sized to fit within the fitting and the seal is sized to form a fluid tight seal with the fitting In further variations, the fluid transfer mechanism includes a flask having a neck ending in a lip defining an opening to the flask. The neck has external threads adjacent the lip. The threads are sized and located to threadingly engage the internal threads on the cap so the cap can be screwed onto the neck. In a further variation, a seal is interposed between the lip of the flask and the cap. The flask contains preferably, but optionally contains Grace's media. The distal end of the spout is optionally offset from a centerline of the skirt.

Optionally, a line is located between the opening in the distal end of the spout and the vent hole. The line is preferably closer to the vent hole than to the distal end of the spout, and preferably the line is visible from the outside of the cap to indicate a fluid level limitation. In the most preferred embodiment, the tubular end has a diameter of about 0.4 inches, and the seal is adjacent the distal end. Ideally, the seal comprises an O-ring seal having a diameter D, and the seal is within a distance of about 2D of the distal end.

There is also provided a method for adding fluid to a bioculture bag having a fitting thereon that is in fluid communication with the inside of the bag. The fitting preferably comprises a Colder Products Company fitting. The method includes placing the fluid in a flask. The flask has a neck with a lip defining an opening at a distal end of the neck. The method includes placing a cap in sealing engagement with the neck and in fluid communication with the opening in the neck. The cap has a spout with a distal end defining a spout opening. The method also includes placing the spout opening in fluid communication with the fitting and sealing the distal end of the spout to the fitting. Finally, the method includes pouring the fluid from the flask through the spout and fitting and into the bag. The method can include less than all the above steps In further variations, the method interposes a seal between a lip of the flask and the cap. It also includes the step of providing a vent hole in the cap. The fluid preferably comprises Grace's media, or a growth media, or an infection fluid. The sealing step preferably includes placing a ring seal around the spout. In further embodiments, the sealing step further comprises placing a ring seal around the spout adjacent the opening in the spout. The sealing step more preferably includes placing a ring seal around the spout, the ring seal having a maximum cross-sectional dimension D with the seal being within 2D of the distal end of the spout. The step of placing the cap in sealing engagement with the neck optionally includes engaging mating threads on the cap and flask to force the lip of the flask against a seal in the cap. The spout is also optionally offset from a longitudinal centerline of the flask. Finally, the cap optionally has a line between the opening in the spout and a vent hole in the cap In a further aspect of this invention, a fermentation container is provided that preferably takes the form of a flask having a bottom with rounded corners and inclined sides forming a cone that narrows to form a neck. A lip at the distal end of the neck defines an opening to the container. The bottom has a series of radially oriented shaped baffles having a generally uniform width, and having inclined surfaces on opposing sides of the width. The height of the baffles decrease as the distance from the center increases. The decrease in height is preferably linear. The baffles thus have a height measured along a centerline of the container that is the smallest toward the corners where the baffles preferably blend into the bottom or corner of the container and that is the greatest toward the center of the container. Preferably, but optionally, there is a generally linear incline between the greatest and smallest height, with an angle α of about 3-12° believed suitable, and with an angle α of about 9° being preferred. The baffles end adjacent to the centerline of the container, but preferably do not abut each other. The ends of each baffle adjacent the centerline incline away from the centerline at an angle β, with an angle β of about 28-48° believed to be suitable, and with an angle β of about 38° being preferred.

The inclination angle θ on the inclination of sides 114a, 114b of the baffles is selected so the media and culture can be rotated in the flask without rupturing the insect and mammalian cells being cultured. The inclination angle along a circumferential direction results in an angle θ of about at about 38-60° or less relative to the vertical axis 18 (FIG. 15) that is believed suitable for at least the depicted embodiment, with an angle θ of about 58° from the horizontal being preferred. The preferred angle relative to the longitudinal axis 18 is about 32°.

A cap is preferably provided over the opening formed by the lip of the container. The cap is preferably, but optionally air permeable. The neck is preferably a wide neck to increase air access and volume and to make it easier to add things to the container and to remove things from the container.

Cell cultures grown in a 2.5 liter flask of the preferred embodiment, when rotated at a speed of about 80-180 RPM, and preferably about 80-100 RPM, are believed to increase cell quantities and reduce growth time.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 1 is a perspective view of a pouring flask;

FIG. 2 is a side plan view of the pouring flask of FIG. 1;

FIG. 3 is a partial sectional view taken along 3-3 of FIG. 2 showing threads;

FIG. 9 is a further, simplified sectional view taken along 7-7 of FIG. 6;

FIG. 10 is a top perspective view of a culture flask;

FIG. 14 is a sectional view taken along 14-14 of FIG. 13; and

FIG. 15 is a bottom plan view of the culture flask of FIG. 10;

DETAILED DESCRIPTION

Figure 5:
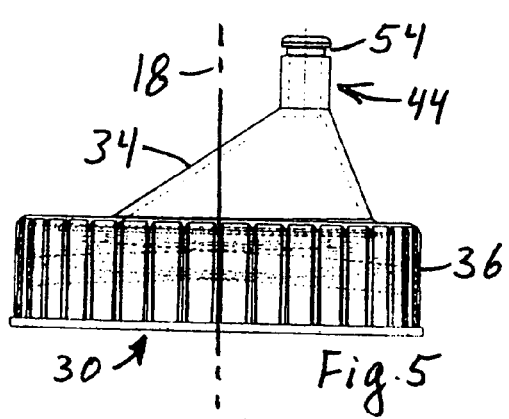
FIG. 5 is a side plan view of the cap of FIG. 4, with the opposing side view being a mirror image thereof.
Figure 4:
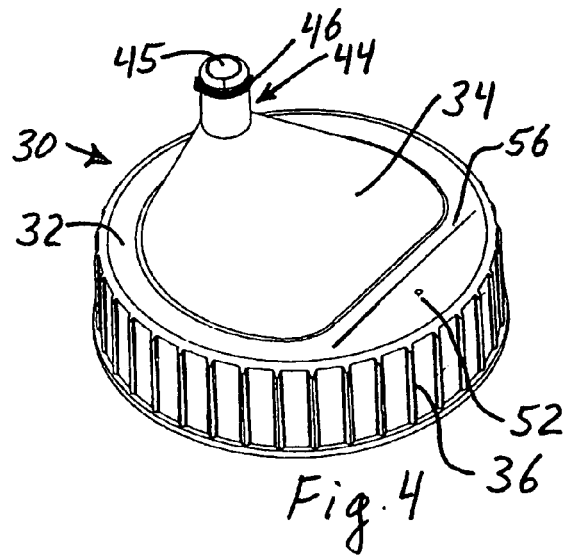
FIG. 4 is a top perspective view of a cap used with the flask of FIG. 1.
Figure 6:
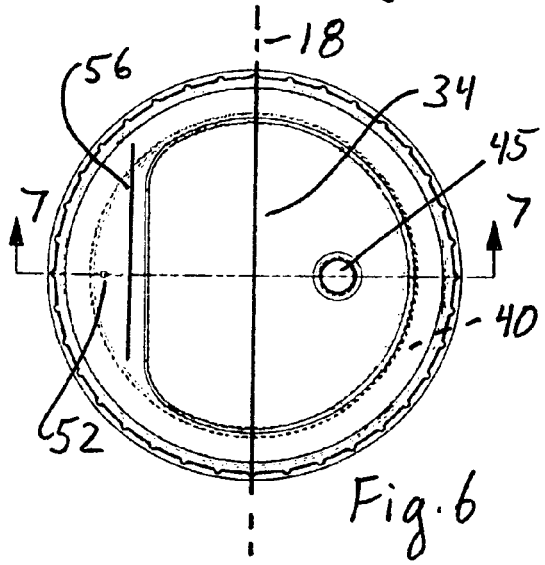
FIG. 6 is top plan view of the cap of FIG. 5
Figure 8:
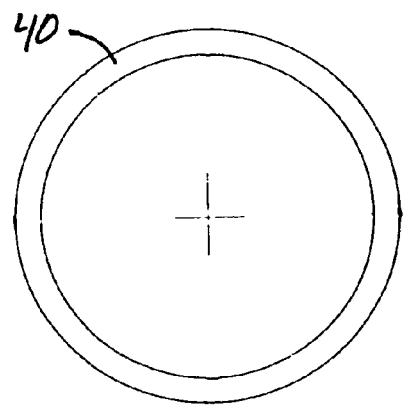
FIG. 8 is a plan view of a ring seal used with the cap of FIG. 4.
Figure 7:
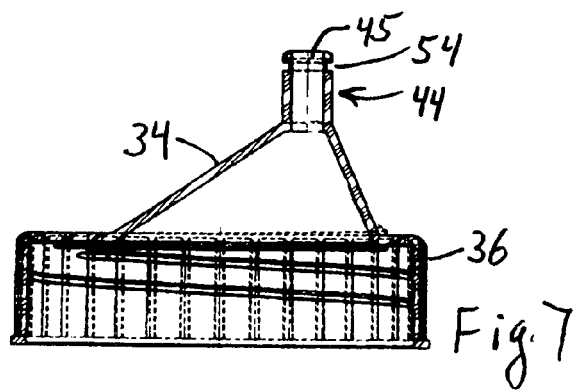
FIG. 7 is a sectional view taken along section 7-7 of FIG. 6.

Referring to FIGS. 1-3, a pouring flask 10 is provided. As used herein, the flask 10 can have any configuration, including cylindrical, globular, or other shapes. In the illustrated embodiment the flask 10 has a bottom 12 with rounded corners 14 joining sides 16. The bottom 14 is preferably, but optionally, slightly curved toward the inside of the flask 10 so that fluid in the flask drains toward the corners 14 when the fluid level in the flask is low. The sides 16 preferably form a conical shape, although other shapes could be used. The conical side 16 is inclined toward a centerline 18 of the flask. The side 16 ends at a neck 20 that is preferably cylindrical in shape, although other shapes could be used. The neck 20 ends at a lip 22. Threads 24 are formed on the outside of the neck, preferably adjacent the lip 22. A single lead continuous thread is believed suitable, but multiple leads are possible, and interrupted threads are desirable for ease of molding. As used herein, the term threads is construed broadly to include bayonet locks and other mechanisms that lock two parts together by rotating one of the parts relative to the other. A stop flange 26 extends outward from the neck, below the threads 24. The flask 10 is preferably made from an injection molded polymer, such as polypropylene. Other materials can be used, as can other forming methods.

The neck 20 is preferably small enough to be held by a single hand. The neck 20 is preferably about 3 inches in diameter (about 75 mm) and about 3 inches long to provide a comfortable gripping area. The diameter and length of the neck can vary. Printed indicia 28 can be provided along the corners 14 and/or side 16 of the flask. The indicia 28 preferably reflect the volume of the flask at different locations along the side of the flask.

Referring to FIGS. 4-8, a cap 30 is provided having a generally planar, annular top 32 containing a spout 34 therein, with a skirt 36 depending from a periphery of the top 32. The skirt 36 has internal threads 38 configured to threadingly engage the threads 24 on the neck 20 of the flask 10.

On the inside of the cap 30, along the annular top 32 is a sealing ring 40. An outer periphery of the sealing ring preferably, but optionally, abuts or is adjacent to the inside of the skirt 36, and the inner periphery of the ring 40 abuts an annular flange 42 depending from the cap, so the sealing ring forms a snap-fit between the flange 42 and the skirt 36. The ring 40 is made of a sealing material, preferably an elastomer such as rubber or Buna. The sealing ring is located to abut the lip 22 when the cap 30 is threaded onto the neck 20 and form a fluid tight seal. The skirt 36 is preferably long enough so the distal end of the skirt abuts the stop flange 26 when the lip abuts the sealing ring 40, in order to prevent over-tightening of the threaded connection and stripping of the threads 34, 38.

Figure 16:
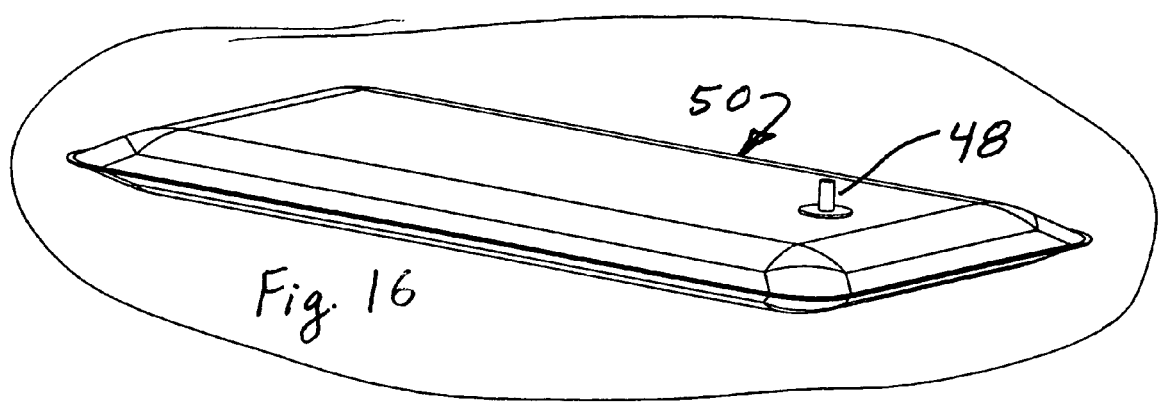
FIG. 16 is a perspective view of a bag and fitting to which the flask and cap of FIG. 1 transfer fluid.

The spout 34 is tapered toward a generally cylindrical, tubular end 44 having an outlet opening 45. The end 44 is preferably, but optionally, offset from the center of the cap 30 and from the centerline 18 of the flask 10 when the cap is threaded onto the flask. The end 44 has a seal 46 configured or adapted to form a fluid tight seal with the standard ¼ inch Could fitting 48 on culture bags 50 (FIG. 16). The fitting 48 is as generally described in U.S. Pat. No. 5,052,725, the complete contents of which are incorporated by reference herein. A vent hole 52 is provided in the cap 30. The vent hole 52 is preferably large enough to allow fluid to continually flow out of the opening 45 in the end 44 and prevent an air lock, but small enough to reduce spillage through the vent hole. The smaller hole also reduces the risk of contamination. A vent hole 52 about 1/16 inch diameter is believed suitable.

Preferably, seal 46 comprises an O-ring or D-ring seal. The seal 46 is optionally held in place on the end 44, as by an adhesive, or a groove 54 encircling the end, with the seal sized to fit within the groove. The seal 46 is preferably adjacent the distal end of the tubular end 44. In the preferred embodiment, the seal 46 has a diameter D and the seal 46 is located a distance of about 1-2D from the distal end of tubular end 44. A single seal 46 is believed suitable, but two or more seals, spaced apart from each other, are also believed suitable.

The end 44 is sized to fit inside the fitting 48 on the bag 50 (FIG. 16), or alternatively could be sized to fit over the outside of a fitting on the bag. An outer diameter of about 0.4 inches (about 10 mm) is believed suitable for the standard Could Products fitting. The size will vary according to the fitting with which the cap 30 and end 44 are to mate.

In use, a growth media such as Grace's media is poured into the open end of the neck 20 of flask 10. The large opening in the neck 20 makes this easy to do manually. The cap 30 is then screwed onto the neck 20 so the lip 22 abuts the seal 40 to seal the cap to the flask. The end 44 is then placed inside the fitting 48 on the bag 50 so the seal 46 forms a fluid tight seal with the fitting. The flask is then tipped or positioned so the growth media flows out through the spout 34 and end 44, into the fitting 48 and bag 50. The vent hole allows air to enter the flask 10 and thus provide a continuous flow. Having an offset spout 34 and end 44 makes it easier to insert the seal 46 into the fitting 48 without spilling. But the offsetting of the spout 34 is optional.

Optionally, a line 56 can be provided on the cap 30 to provide a visual reference on how to tip the flask. The line 56 is visible to the user, and located between the end 44 and the vent hole 52. As the flask is inclined the fluid level in the flask abuts the cap 30, and by keeping the fluid below the line the vent hole 52 is kept open. Preferably, but optionally, the line 56 can coincide with the juncture of an inclined portion of the spout 34 and a flat portion of the top 32.

The ability to manually fill the flask 10 with growth media and manually couple the flask and cap to the fitting 48 greatly reduces the time to fill the bag 50, as well as significantly reducing the spillage compared to prior manual filling procedures. The flask spout 34 and end 44 provide a fast way to fill the bag 52. Using pumps to fill the bags 52 can take hours, whereas the cap 30 can empty the flask 10 in a matter of minutes. Fluid transfer rates of about 1 liter per minute are believed possible. The flask 10 is preferably 2-3 liter in volume for ease of handling. Smaller or larger flasks could be used, but with some effect on fill time and ease of manual handling. The flask 10 thus allows a single person to fill the bag 10 with the desired amount of growth media, in a shorter time, with less spillage, than previously.

The above embodiment is configured to connect to the standard, ¼ inch diameter Colder Products fitting, but the same design can be adapted to work with the smaller ⅛ inch diameter (about 4 mm) also provided on these bags 52 for the introduction of infections to the bag. The same design could be adapted to work with larger diameter fittings.

Referring to FIGS. 10-15 in a preferred embodiment a different container is provided. The container 110 has a bottom 112 with a plurality of baffles 114 thereon. The bottom 112 has rounded corners 116 joining a sidewall 18 that is preferably, but optionally tapered toward a central longitudinal axis 120 in one or more angles of inclination. The sidewall 118 joins a neck 122 having a lip 124 defining an opening 126 at a distal end of the neck and container. In the depicted embodiment the sidewall 118 has a lower portion 118a with sidewalls generally parallel to the longitudinal axis 120, a middle portion having sidewalls 118b slightly inclined toward the longitudinal axis 120, and an upper portion having sidewalls 118c more steeply inclined toward the longitudinal axis 120 and mating with the bottom of the neck 122.

Figure 13:
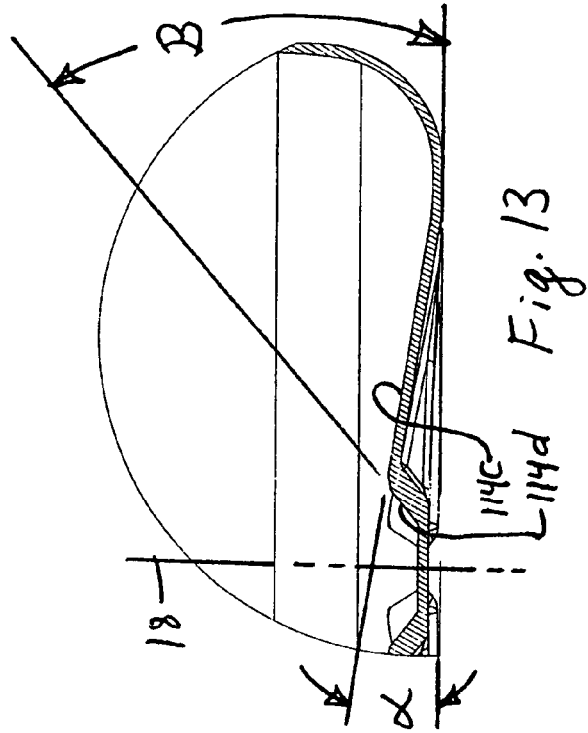
FIG. 13 is a sectional view taken along 13-13 of FIG. 10.
Figure 12:
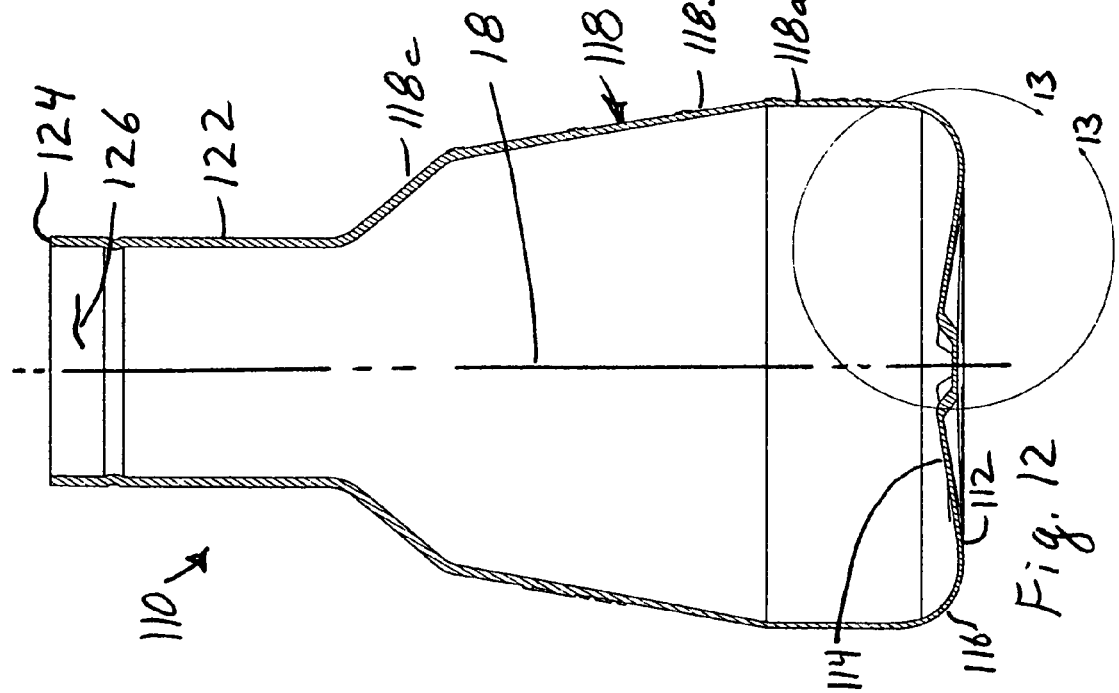
FIG. 12 is a side plan view of the culture flask of FIG. 10.

Referring to FIG. 13, as used herein, inward means toward the longitudinal axis 120 while outward refers to the opposing direction. The term up or upper refers to the direction from the bottom 112 toward the lip 124, and down or lower refers to the opposite direction.

The dimensions of the outside of the container 110 will vary, as will the specific dimensions of the baffles 114. But the general shape of the baffles will be as described herein or as otherwise configured to flow fluid over the baffles enough to aerate the fluid while not rupturing the cell walls. A 2.5 liter flask is described for ease of illustration, but the size will vary with the particular use of the container 110.

The 2.5 liter flask 110 has a bottom diameter of about 6 inches (about 150 mm) and an overall height of about 11 inches (28 cm), with a neck 122 about 3 inches (75 mm) long and 3 inches (75 mm) in diameter. The container is preferably made of glass or a polymer, such as polypropylene. Injection molded or blow molded containers are preferred so they can be disposable and reduce contamination arising from reuse.

Figure 11:
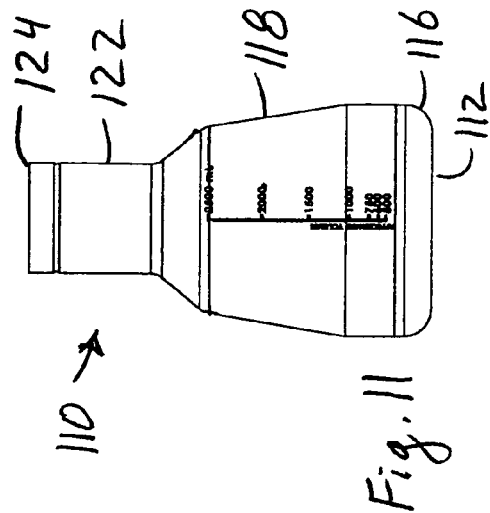
FIG. 11 is a bottom perspective view of the culture flask of FIG. 10.

Referring to FIGS. 11 and 13-5, the baffles 114 are shaped to aerate and mix the culture while not rupturing the cells in the culture. The baffles are configured to avoid turbulent flow sufficient to form bubbles. Laminar flow is preferred, but even high speed laminar flow can create shear forces sufficient to rupture the cell walls. Thus, for a specified rotational speed of use for the flask 110, the baffles 114 are preferably configured to achieve laminar flow with insufficient shear to rupture the cell walls.

In the depicted embodiment, baffles 114 are pie shaped segments formed by a bottom 112 that extends inward toward lip 124 but with generally rectangular shaped recesses 115 are in a generally horizontal plane on which the container 10 rests. The recesses 15 extend outward from centerline 120. The number of baffles can vary, but an even number of symmetrically arranged baffles are preferred. Six baffles 114 are shown, separated by six recesses 115 with the recesses spaced about 60° apart. Four baffles 114 are also believed usable, separated by four recesses spaced about 90° apart.

The container 110 is typically rotated in a continuous direction, preferably clockwise, and the baffles will be described with that orientation. During use the actual orientation can change at the control of the user—provided the equipment accommodates the change in direction. Each baffle 114 thus has a leading edge 114a, a trailing edge 114b, and a middle portion 114c which joins the leading and trailing sides. The leading and trailing sides 114a, 114b are inclined at an angle θ that is preferably about 38-60° relative to the horizontal when the bottom 112 is resting on the horizontal. An angle θ of about 32° is believed preferable for rotational speeds of about 80-180 RPM with a speed of about 250 RPM or lower, with speeds of 80-180 RPM being preferred, and speeds of about 80-100 RPM being most preferred. Higher speeds could be used, but the angle θ would have to be adjusted to avoid shear rupture of the cells. At sufficiently high speeds the laminar shear force in the culture fluid can rupture the cells. Thus, the shear in the fluid is advantageously maintained below about 500 dynes/cm$^2$ and preferably maintained below about 50 dynes/cm$^2$. Thus, the baffles are preferably configured relative to the rotations speed to maintain the fluid shear at levels low enough to avoid rupturing the cells in the culture.

The sides 114a, 114b are generally radially oriented and extend away from centerline 120. The middle portion 114c is generally flat but could be slightly convex. The baffles 114 are preferably pie shaped segments formed by the recesses 115, but the shape could vary.

The angle θ at which the sides 114a, 114b are inclined is selected so the cells in the culture do not rupture when the container 110 is rotated at a generally constant speed for several hours, preferably for over 48 hours. The normal culture growth is from 48-72 hours after the culture is infected, before the cells are harvested. The agitation causing aeration must be very mild because the formation of bubbles will typically reflect the rupture of cell walls. It is believed the cells adhere to the bubbles and it is known that the bursting of the bubble can rupture the cell walls. If the rotation speed increases, the angle θ may decrease in an effort to reduce the shear force on the cells in the culture. Thus, the rotational speed and baffles cooperate to maintain the shear in the culture fluid below about 500 dynes/cm$^2$ and preferably maintained below about 50 dynes/cm$^2$. The data predicting the permissible shear is of questionable accuracy, and the permissible shear can vary with the cell type, so higher shear values may be permitted as long as the cells are not ruptured in sufficient quantities to unacceptably degrade the yield of the culture.

The separation between the raised baffles 114 can also affect the aeration and agitation of the culture fluid. The recesses 115 form the space between baffles, and the recesses have a trapezoidal cross section with the smallest side of the trapezoid formed by the bottom 112 and the sides 114a, 114b forming the sides of the trapezoidal cross-section. The recesses 115 are generally rectangular in shape with a depth greatest adjacent the centerline and the smallest near the corners 116. A recess about 0.3 inches wide at the smallest, is believed suitable for the 2.5 liter flask.

The inclined sides 114a and 114b are preferably inclined the same amount, but in opposite directions so the culture fluid flows gently up the leading side 114a, across the top or middle portion 114c, and down the trailing side 114b. The culture fluid then flows across the recess 115, up the next leading edge 114a, over the next top 114c and down the trailing edge 114b into the next recess 15. The undulating motion caused by the baffles and recesses aerates the culture fluid without rupturing cell walls.

In a rotational system rotating about centerline 120, the speed of the culture fluid is lowest at the rotational axis 120, and increases linearly with the radial distance from that axis 120. Friction between the culture fluid and the container 10 prevent the fluid from rotating at the exact speed of the container. But because the culture fluid at the radially distant corners 116 moves at a greater speed than the fluid adjacent the centerline 120, the height of the baffle 114 decreases toward the corners 116 in order to avoid over-agitating the fluid and damaging the cells in the culture. The baffles 114 are highest adjacent the centerline 120.

The baffles 114 thus have a height that is lowest adjacent the corners 116 and greatest adjacent the centerline 120. Adjacent the corners 116 the baffles preferably, but optionally, blend smoothly into the bottom 112 and corners 116. Advantageously the baffles 114 end before the corners 116, and preferably end a distance D before outer circumference of the corners 116 is reached, where the distance D is about ⅓ the distance from the centerline 120 to the outermost circumference of the corner 116. In the illustrated embodiment, the bottom is about 6 inches diameter and the baffles 114 end about 1 inch before the outermost portion of the corners 116.

Baffles having the middle or top portion 114c inclined at about 5-12° are believed suitable for a rotational speed of about 80-180 RPM. An inclination angle of about 9° is believed preferable for the illustrated embodiment, with the preferred speed of rotation being about 80-100 RPM.

Adjacent the centerline 120, the baffles are the highest, but preferably they end before reaching the centerline so there is an optional open area at the centerline. An open area about ⅛ the diameter of the container 110 is believed suitable. Preferably, but optionally, the interior ends 114d of baffles 114 are inclined away from the centerline 120 at an angle β of about 28-48° to the horizontal, with an angle β of about 38° to the horizontal being preferred. The juncture between the inclined end 114d and the top 114c and sides 114a, 114b, is rounded sufficiently to reduce, and preferably entirely avoid, damage to the cells during rotation of the container 110.

For the depicted embodiment, each segment 114 is thus about 0.2-0.3 inches (about 5-8 mm) high at end 114d, and tapers in a generally straight line to blend with the generally flat bottom 112 at a distance about ⅔ the radius of the container and adjacent the corners 16. There are six baffles 114, each having a pie shape, and separated by a generally rectangular recess 115, with the recess passing through the centerline 120 to form a recess at the centerline 120.

In use, a growth media is placed in the flask 110, typically a volume about ⅓ the total volume of the flask. The growth media entirely covers the baffles 114. Indeed, the maximum height of the baffles 14 from the horizontal plane of bottom 112, measured along centerline 120 is preferably about ⅓ or less the height of the fluid in the flask 110. The height of baffle 114 is advantageously about ⅕ to 1/10 the fluid height.

The cell culture is added to the growth media before or after the media is placed in the flask 110. A representative cell includes 10-20 micron diameter insect cells or mammalian cells greater than 1-10 microns in diameter, each of which require low shear to avoid rupturing the cells. Foam in the fluid media will rupture the cell walls. The wide opening 126 allows easy addition and removal of fluids and cell cultures to the flask.

The flask 110 is then clamped into a rotational device which is known in the art and not described herein. The inclined portion of sidewalls 118 cooperate with clamping or holding mechanisms on the rotational device to center and hold the flask 110 during rotation. The flask and contents are then rotated at about 80-180 RPM. The fluid undulates over the baffles 114 to stir, mix and slightly aerate the fluid media without rupturing the cell walls.

When a desired cell density is achieved, the cells are infected with a specified virus. The cells are further cultured for a time typically corresponding to 48 to 72 hours before the cells are harvested. During that time other fluids can be added through the opening 126. If the cell viability drops below 90%, the culture may not be suitable for the intended use.

To reduce contamination during this culture growth, the opening 126 is preferably covered by a cap 30 as described above regarding FIGS. 4-6. To transfer the culture, the cap 30 is used.

The above description is given by way of example, and not limitation. Given the above disclosure, one skilled in the art could devise variations that are within the scope and spirit of the invention disclosed herein, including various ways of sealing the end 44 to the fitting 48. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A fluid transfer mechanism for use with a bioculture container having a fitting thereon in fluid communication with the inside of the bioculture container, comprising:

a cap having a spout with an opening in a distal end of the spout, the cap having a peripheral cylindrical skirt with internal threads on the skirt, and a vent hole in the cap, the spout having a tubular end in which the opening is formed, with a seal on an outward facing side of the distal end and encircling the tubular end, the tubular end sized to fit within the fitting and the seal sized to form a fluid tight seal with the fitting.

2. The mechanism of claim 1, further comprising a bioculture flask having a neck ending in a lip defining an opening to the flask, the neck having external threads thereon adjacent the lip, the threads being sized and located to threadingly engage the internal threads on the cap with the cap being screwed onto the neck.

3. The mechanism of claim 2, wherein a seal is interposed between the lip of the flask and the cap to provide a fluid tight seal between the cap and the flask.

4. The mechanism of claim 2, wherein the flask contains Grace's media or growth media.

5. The mechanism of claim 1, wherein the distal end of the spout is offset from a centerline of the skirt.

6. The mechanism of claim 1, further comprising a line located between the opening in the distal end of the spout and the vent hole, and closer to the vent hole, the line being visible from the outside of the cap to indicate a fluid level limitation.

7. The mechanism of claim 1, wherein the tubular end has a diameter of about 0.4 inches.

8. The mechanism of claim 1, wherein the seal is adjacent the distal end.

9. The mechanism of claim 2, wherein the seal comprises an O-ring seal having a diameter D, and the seal is within a distance of about 2D of the distal end.

10. The mechanism of claim 1, wherein the bioculture container comprises a flask that has a bottom with baffles that are inclined radially and inclined in a circumferential direction, with the radial inclination being at an angle of about 3-12° from the horizontal toward the centerline and with the circumferential inclination being at an angle of about 38-60° on a leading side and about the same on a trailing side.

11. The mechanism of claim 1, wherein the bioculture container comprises a flask that has a bottom with curved corners joining sidewalls, the bottom having baffles that are inclined radially from a maximum height adjacent the centerline and a minimum height toward the corners, and an angle of inclination selected so the fluid shear in a culture placed in the flask during normal use at a rotational speed of about 80-180 RPM is below about 500 dynes/cm$^2$.

12. The mechanism of claim 1, wherein the bioculture container comprises a flask that has a bottom containing baffle means for agitating the culture during use of the flask.

13. A method for adding fluid to a bioculture container having a fitting thereon that is in fluid communication with the inside of the bioculture container, comprising:

placing the fluid in a bioculture container, the bioculture container having a neck with a lip defining an opening at a distal end of the neck;

placing a cap in sealing engagement with the neck and in fluid communication with the opening in the neck, the cap having a spout with a distal end defining a spout opening;

placing the spout opening in fluid communication with the filling;

sealing the distal end of the spout to the fitting using a ring seal on an outward facing side of the spout to seal against the fitting;

pouring the fluid from the bioculture container through the spout and fitting and into the bioculture container.

14. The method of claim 13, further comprising interposing a seal between a lip of the bioculture container and the cap.

15. The method of claim 13, further comprising the further step of providing a vent hole in the cap.

16. The method of claim 13, wherein the fluid comprises Grace's media.

17. The method of claim 13, wherein the fluid comprises a growth media.

18. The method of claim 13, wherein the sealing step further comprises placing the ring seal in a groove around the spout with the fitting having an inner surface with a circular cross-section into which the spout is inserted and ring seal sized to engage that inner surface of the fitting.

19. The method of claim 13, wherein the sealing step further comprises placing a the ring seal around the outside of the spout adjacent the opening in the spout.

20. The method of claim 13, wherein the sealing step further comprises placing the ring seal around the outside of the spout, the ring seal having a maximum cross-sectional dimension D with the seal being within 2D of the distal end of the spout.

21. The method of claim 13, wherein the step of placing the cap in sealing engagement with the neck comprises engaging mating threads on the cap and bioculture container to force the lip of the bioculture container against a seal in the cap.

22. The method of claim 13, wherein the spout is offset from a longitudinal centerline of the bioculture container.

23. The method of claim 13, wherein the cap has a line between the opening in the spout and a vent hole in the cap located to indicate a fluid level during transfer of fluid through the spout.

24. The mechanism of claim 1, wherein the tubular end of the spout comprises a cylindrical tube offset from a centerline through the center of the skirt, the cylindrical tube ending a distance from the skirt with a surface tapered outward to join the skirt to the cylindrical tube, the vent being offset from the centerline toward a side of the skirt that is opposite the cylindrical tube.

* * * * *